(12) United States Patent
Imai et al.

(10) Patent No.: US 8,286,628 B2
(45) Date of Patent: Oct. 16, 2012

(54) DRUG EJECTION APPARATUS, ESTIMATION OF EJECTION PERFORMANCE THEREOF, AND METHOD OF DRUG EJECTION

(75) Inventors: Mitsuru Imai, Chichibu (JP); Keisuke Kawahara, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 813 days.

(21) Appl. No.: 12/356,343

(22) Filed: Jan. 20, 2009

(65) Prior Publication Data

US 2009/0188494 A1 Jul. 30, 2009

(30) Foreign Application Priority Data

Jan. 25, 2008 (JP) .................................. 2008-014458

(51) Int. Cl.
*A61M 11/00* (2006.01)
(52) U.S. Cl. ......... 128/200.14; 128/200.23; 128/203.12; 128/203.15
(58) Field of Classification Search ............. 128/200.14, 128/200.16, 200.23, 200.24, 202.22, 203.12, 128/203.15, 203.26

See application file for complete search history.

(56) References Cited

U.S. PATENT DOCUMENTS

| | | | | |
|---|---|---|---|---|
| 2004/0107961 A1* | 6/2004 | Trueba | ...................... | 128/200.16 |
| 2004/0163641 A1* | 8/2004 | Tyvoll et al. | .............. | 128/200.23 |
| 2005/0172957 A1* | 8/2005 | Childers et al. | ........... | 128/200.23 |
| 2006/0131350 A1* | 6/2006 | Schechter et al. | ............. | 222/645 |
| 2007/0227534 A1 | 10/2007 | Nobutani et al. | ........ | 128/200.14 |

* cited by examiner

*Primary Examiner* — Lynne Anderson
*Assistant Examiner* — Kathryn D Ditmer
(74) *Attorney, Agent, or Firm* — Fitzpatrick, Cella, Harper & Scinto

(57) ABSTRACT

A drug ejection apparatus comprises a drug ejection assembly having an ejection port and an element for generating energy for ejecting a drug through the ejection port, a drug container connected with the drug ejection assembly for holding the drug, a pressure sensor unit for sensing a pressure change in the inside of the drug container in correspondence with ejection of the drug through the drug ejection assembly, and a drive control unit for deciding driving conditions of the element for ejecting a prescribed amount of the drug by reference to an output level of the pressure sensor unit on driving the element under prescribed conditions.

6 Claims, 12 Drawing Sheets

DRUG EJECTION APPARATUS, ESTIMATION OF EJECTION PERFORMANCE THEREOF, AND METHOD OF DRUG EJECTION

BACKGROUND OF THE INVENTION

1. Field of the Invention

The present invention relates to a drug ejection apparatus which is portable and is applicable to an inhalation apparatus for inhalation of a drug by a user. The present invention relates also to a method for estimating the ejection performance of the drug ejection apparatus.

2. Related Background Art

Inhalation apparatuses have been developed which allow a user to inhale, through a mouthpiece, fine liquid drug droplets ejected based on the principle of an inkjet system (US Patent Application Publication No. 2007-0227534). Such an inhalation apparatus is capable of spraying precisely a prescribed amount of the drug in a uniform particle diameter.

Such a drug ejection apparatus is constituted basically of an ejection head having an ejection energy-generating element like a heating element and a drug tank for holding a drug to be fed to the ejection head. For efficient absorption of the ejected liquid drug by a lung of a user, the liquid droplets should have a fine diameter, as fine as several microns, and for the ejection of the fine liquid droplets, the orifice of the ejection head should have an orifice diameter of several microns.

Owing to the extremely fine diameter of the orifice, when one and the same ejection head is used for several times of inhalation, the liquid drug remaining after the preceding drug ejection can dry to become viscous and can stick to the inside wall of some of the orifices (nozzles) to clog the orifice. With repetition of the use of the ejection head, the number of the orifices available for the subsequent drug ejection can be decreased, whereby the amount of the drug ejected for the inhalation can become less than the intended amount even when the head is driven under the same conditions for the same period.

Therefore, when the drug is ejected under fixed driving conditions by assuming that the ejection can be constant under the fixed conditions, the intended amount (prescribed by a medical doctor) of the drug can not be ejected.

Desirably, the amount of the drug ejected through the ejection head is measured precisely in-situ, and the ejection is stopped on ejection of the intended amount of the drug. However, this is impossible practically.

Otherwise, the clogged nozzle can be recovered by suction with a pump in a manner as conducted in ink-jet printers. However, this is not suitable for the inhalation apparatus, since the inhalation apparatus, which is carried always by the user, should be small and lightweight and the suction mechanism like a pump is not preferred, and the drug is generally more expensive than the ink and discard of the drug by suction is undesirable.

SUMMARY OF THE INVENTION

The present invention provides a drug-ejection apparatus which is capable of ejecting a drug in a constant ejection amount per one ejection regardless of the repetition times of ejection.

The present invention is directed to a drug ejection apparatus comprising: a drug ejection assembly having an ejection port and an element for generating energy for ejecting a drug through the ejection port, a drug container connected with the drug ejection assembly for holding the drug, a pressure sensor unit for sensing a change of the inside pressure of the drug container caused in correspondence with an amount of the drug ejected through the drug ejection assembly, and a drive control unit for deciding driving conditions of the element for ejecting a prescribed amount of the drug by reference to an output level of the pressure sensor unit on driving the element under prescribed conditions.

The apparatus can comprise further a pressurizing unit for pressurization of the drug container to decrease the volume of the drug container to moderate decrease of the inside pressure caused by ejection of the drug.

The pressurization of the drug container by the pressurizing unit can be stopped during driving of the element under prescribed conditions.

In the drug ejection apparatus, any of the driving conditions of the element including ejection frequency, ejection pulse width, driving voltage decided by the drive control unit can be adjusted so that the ejection period is not longer than a prescribed period.

The apparatus can comprise a sensor for sensing inhalation by a user, and driving of the element is stopped when the inhalation by the user comes to be not sensed by the sensor.

The apparatus can comprise a unit for measuring the amount of the ejected drug, and the drive control unit decides the conditions for driving the element for ejecting the drug in an amount corresponding to the difference of the amount of the ejected drug from the prescribed amount of the drug on stopping the drive of the element.

The present invention is directed to a method for estimating ejection performance of a drug ejection apparatus, having a drug ejection assembly having an ejection port and an element for generating energy for ejecting the drug through the ejection port, and a drug container connected to the drug ejection assembly for holding the drug, wherein the performance of ejection of the drug is estimated from the change of the inside pressure of the drug container caused by driving of the element under prescribed driving conditions.

The present invention is directed to a method for ejecting a drug employing a drug ejection apparatus, having a drug ejection assembly having an ejection port and an element for generating energy for ejecting the drug through the ejection port, and a drug container connected to the drug ejection assembly for holding the drug, wherein the method comprises: a first step of ejecting the drug through the drug ejection port with the volume of the drug container fixed, a second step of sensing a pressure change in the drug container corresponding to the amount of the drug ejected in the first step, a third step of deciding conditions of driving the element for ejecting the drug in a prescribed amount, and a fourth step of ejecting the drug through the drug ejection assembly under the driving conditions decided in the third step.

The ejection performance of the ejection head of the drug-ejection apparatus of the present invention can be estimated from pressure change in the drug container. Based on the estimation, the driving conditions of the ejection head can be adjusted to keep the intended amount of the ejection in every ejection operation.

Other features and advantages of the present invention will be apparent from the following description taken in conjunction with the accompanying drawings, in which like reference characters designate the same or similar parts throughout the figures thereof.

DETAILED DESCRIPTION OF THE INVENTION

Figure 1:
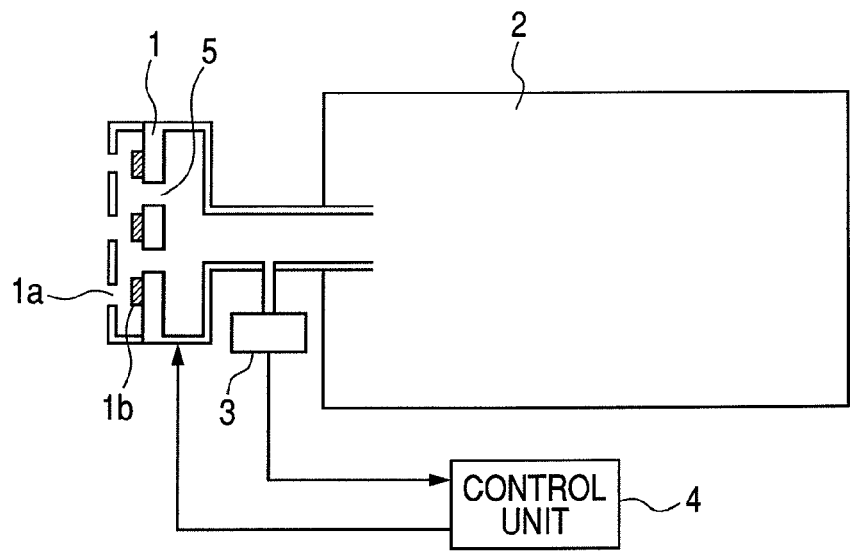
FIG. 1 illustrates schematically a part of a drug-ejection apparatus of the present invention.

Preferred embodiments of the present invention will now be described in detail in accordance with the accompanying drawings.

In the description below, the same reference numerals are used for denoting corresponding constitution elements without repeating the definition.

FIG. 1 illustrates schematically a part of a drug-ejection apparatus of the present invention. Drug ejection assembly (ejection head) 1 comprises ejection port (nozzle) 1a for ejecting the drug and element 1b for generating energy for drug ejection through ejection port 1a. Ejection energy-generating element 1b applies the ejection energy to the drug introduced through drug feed port 5 to eject the drug through ejection port 1a.

Drug container 2 for storing the drug to be ejected is connected to drug ejection assembly 1, and is intercepted from outside air except ejection port 1a. Ejection of the drug through ejection port 1a results in decrease of the amount of the drug stored in the drug container 2, which causes a pressure difference between the inside and the outside of the drug container 2. The negative pressure in drug container 2 is in a linear relation with the amount of the drug ejected through drug ejection assembly 1, when the inside volume of drug container 2 is fixed. In this drug-ejection apparatus, pressure sensor 3 as the pressure measuring unit is joined to drug container 2 for measuring the inside pressure of drug container 2. This pressure sensor 3 measures the pressure change in the inside of drug container 2, corresponding to the amount of the drug ejected through drug ejection assembly 1.

The present invention is characterized in that the ejection performance of the ejection head is estimated by converting the total amount of the drug ejection in a certain period to the change of the inside pressure in drug container 2 in that period. The estimated ejection performance is reflected to the conditions for the subsequent ejection to eject the drug in a constant amount.

Firstly, the drug ejection is started by keeping the inside volume of drug container 2 fixed during a certain period. The estimated pressure change in the first-time ejection in which the ejection performance is not deteriorated has been memorized preliminarily in a memory unit of the inhalation apparatus. After several times of the ejection operation, the pressure change by drug ejection becomes less. This decrease of the pressure change suggests deterioration of the ejection performance. Therefore the ejection conditions is adjusted according to the output level of pressure sensor 3, namely the measured pressure change, by lengthening the ejection period or increasing the driving frequency to keep the intended ejection amount. Signals for ejection are transmitted to ejection head 1 from drive control unit 4 regarding the initial ejection for estimating the ejection performance and the later ejection under the adjusted ejection conditions.

The drug ejected in the initial ejection for estimating the ejection performance may be used for inhalation, or may be used as an extra ejection not for the inhalation. For example, the intended amount of the inhaled drug is taken as 100 parts. When the drug ejected in the initial ejection is not used for the inhalation, the conditions for the subsequent ejection are decided to eject 100 parts according to the estimated ejection performance. On the other hand, when the drug ejected in the initial ejection is used for the inhalation, the initial ejection is conducted to eject 20 parts of the drug by assuming that the ejection performance is not deteriorated, and, if the actually ejected amount is 15 parts (estimated by the pressure change), the conditions for the following ejection are adjusted to eject the remaining 85 parts of the drug.

As described above, the method of drug ejection of the present invention comprises at least the following steps: a first step of ejecting the drug from drug ejecting assembly 1 with the volume of drug container 2 kept fixed; a second step of measuring the change of the inside pressure of drug container 2 corresponding to the amount of the drug ejected in the first step; a third step of adjusting the driving conditions of ejection energy-generating element 1*b* for ejecting an intended amount of the drug from the pressure change in the second step; and a fourth step of ejecting the drug from drug-ejection assembly 1 under the driving conditions adjusted in the third step.

Drug ejection assembly (ejection head) 1 has ejection energy-generating element 1*b* such as an electro-thermal transducer element for giving a thermal energy to the drug, and an electromechanical transducer element for giving a mechanical energy to the drug, but the energy-generating element is not limited thereto. The method for drug ejection includes a thermal jet system which employs an electro-thermal transducer element to give a thermal energy to a drug for ejection, and a piezo jet system which employs an electro-mechanical transducer element (e.g., a piezo element) to give a mechanical energy (e.g., vibration energy) to the drug for the ejection. The ejection system can be selected suitably for the kind of the drug.

With the thermal jet system, the diameter of the ejection port, the heat quantity of the ejection heat pulse, and the size precision of the micro-heater as the electro-thermal transducer element can be selected for higher reproducibility. Thereby the liquid droplet diameter distribution can be narrowed. The production cost of the head of this system is low, so that this system is highly applicable to a small-sized apparatus which requires frequent exchange of the head. The ejection principle of the thermal jet system is particularly suitable for a portable simple drug-ejection apparatus.

In this specification of the present invention, the term "ejection operation period" or "ejection period" signifies the period, in one use of the apparatus, from the time of application of the first pulse to the energy-generating element to the time of application of the last pulse, namely the period of applying a pulse sequence for ejection energy generation. The term "ejection frequency" signifies the number of the pulse signals applied to the ejection energy-generating element per unit time. This term is occasionally called a "driving frequency". The term "pulse width" signifies an energization time for one pulse signal application. The term "driving voltage" signifies the voltage applied to the ejection energy-generating element. With the above driving conditions (ejection conditions) of the ejection head kept fixed, the ejection energy applied to the drug is unchanged, but the amount of the drug actually ejected tends to decrease with clogging of the nozzle. The total amount of the ejected drug can be changed by changing suitably one of the above-mentioned ejection conditions. The amount of the ejected drug may be changed by changing two or more of the above conditions combinedly for obtaining a necessary administration dose.

The construction of drug container (drug tank) 2 is described specifically later in Examples. The construction is described briefly here. The main body of the drug tank may be a glass vessel having open ends, and the one end may be plugged with a rubber stopper or the like: the other end is connected to ejection head 1.

Figure 2:
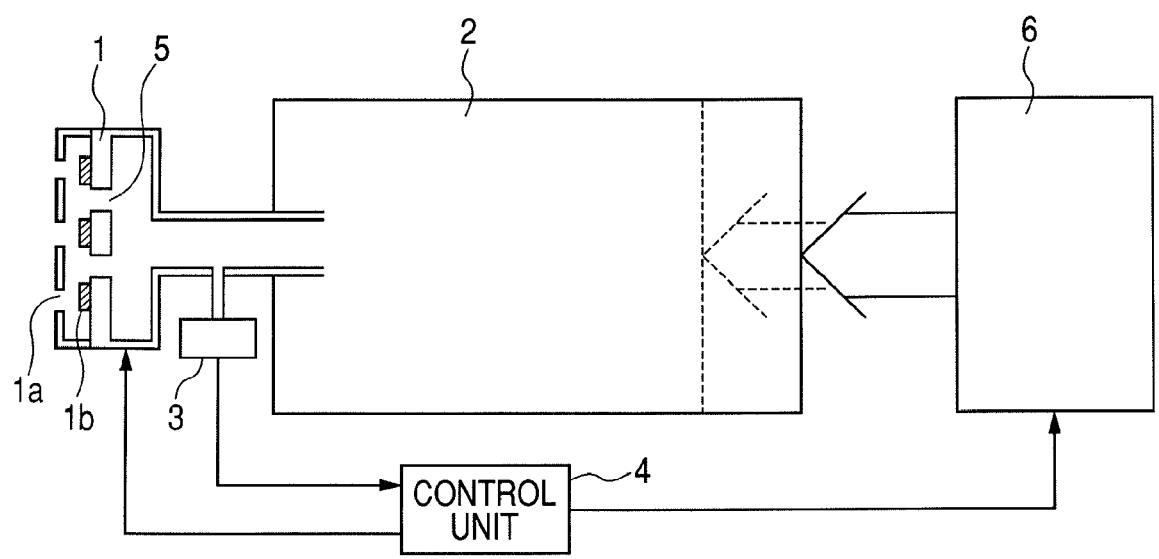
FIG. 2 illustrates schematically a part of another drug-ejection apparatus having additionally a pressurizing unit 6 for pressurizing a part of the drug container 2.

FIG. 2 illustrates schematically a part of another drug-ejection apparatus having additionally a pressurizing unit 6 for pressurizing a part of the drug container 2.

The pressure in a tightly closed drug-container 2 like a glass container decreases with progress of the ejection of the drug to cause a decrease of the ejection amount of the drug, and finally the ejection can be stopped. To mitigate the pressure drop caused by the drug ejection, pressurizing unit 6 is preferably employed to decrease the inside volume of the container. For the drug container constituted of a glass container and a rubber stopper, a rubber stopper pushing mechanism is useful as pressurizing unit 6: the rubber stopper is allowed to slide into the glass container to mitigate the negative pressure.

With such a constitution, during initial stage of the ejection, the rubber stopper is preferably immobilized to keep the volume of the drug container. For example, during the initial stage of the ejection, the pressurization by pressurizing unit 6 may be stopped. Thereby, the rubber stopper is kept in the position by the static friction between the glass container and the rubber stopper during the initial stage of the ejection. Thereafter, the rubber stopper may be moved at a constant rate in accordance with the decrease of the amount of the drug.

The drug employed in the present invention includes not only medical compounds exhibiting pharmacological or physiological action, but also charming taste components, charming odor components, dyes, and pigment. The drug may contain an additive.

(Drug Ejection Apparatus)

Figure 3:
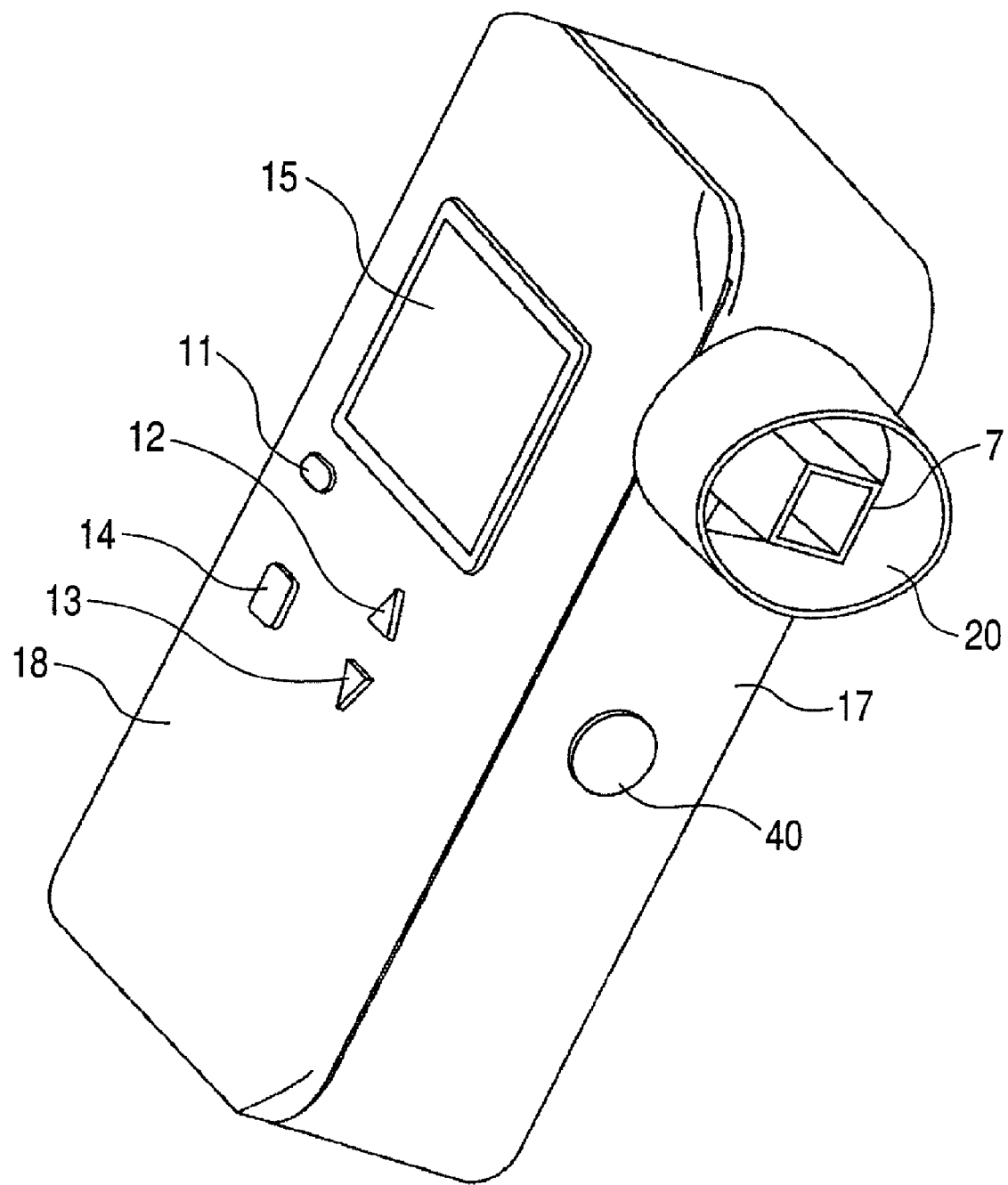
FIG. 3 illustrates perspectively an external appearance of an inhalation apparatus of the present invention for inhalation of a drug by a user.

FIG. 3 illustrates perspectively an external appearance of an inhalation apparatus of the present invention for inhalation of a drug. Housing case 17 and access cover 18 constitute the casing of the main body. Hook 19 (FIG. 4) is fixed to the hook-receiver functioning combinedly with spring-energized unlocking button 40 for closing access cover 18 during the use. For opening access cover 18, unlocking button 40 is pressed to unlock the hooking and open access cover 18 by aid of the spring not illustrated in the drawing. Display unit 15 is provided on access cover 18 for displaying the dose, time, error, and so forth. For setting by the user, are provided menu-switching button 11, and setup buttons 12 to 14: up-button 12, down-button 13, and enter button 14.

Figure 4:
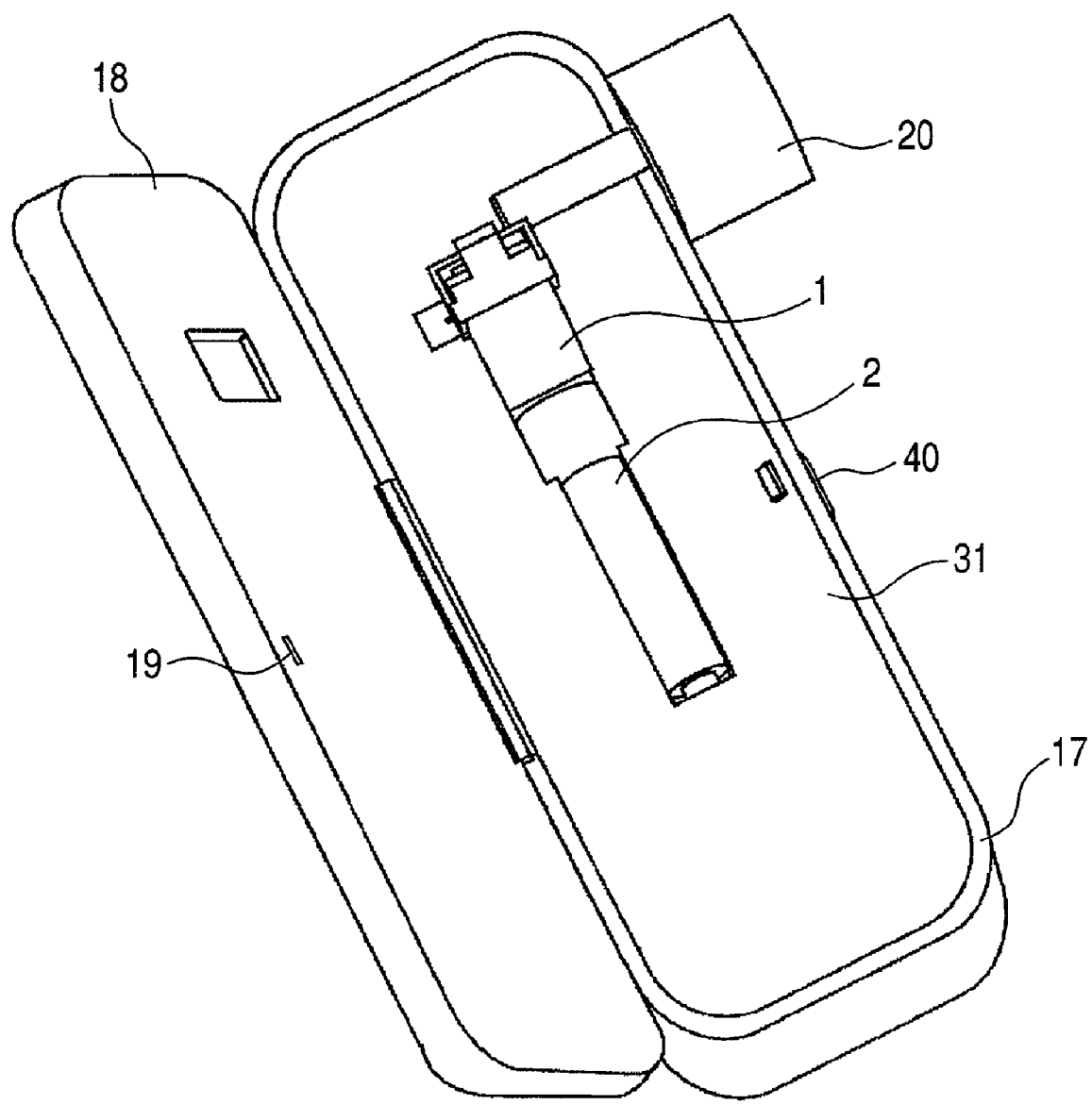
FIG. 4 illustrates the inhalation apparatus illustrated in FIG. 3 with access cover 18 opened.

FIG. 4 illustrates the inhalation apparatus illustrated in FIG. 3 with access cover 18 opened. By opening access cover 18, ejection head 1 as the drug ejection assembly and drug tank 2 as the drug container are uncovered, both of which are demountable from the main body. Ejection head assembly 1 ejects the drug into air flow path 7. The user can inhale the drug ejected into the air flow path by breathing in the air through inhalation port (mouthpiece) 20. In this embodiment, inhalation port 20 and air flow path 7 are integrated. Inhalation port 20 is renewed every time of the inhalation or the used integration port after the inhalation is washed and reused. Ejection head 1 and drug tank 2 are exchanged when the amount of the drug in drug tank 2 becomes less than the one inhalation dose. For example, the apparatus has a counter for counting the amount of the ejected drug. This counter is capable of counting the remaining amount. Thereby, the time of container exchange can be notified to the user, the user is urged to exchange the drug container, or the ejection can be stopped until the completion of the exchange. Drive portion-protecting cover 31 protects the inside mechanism of the inhalation apparatus not to be touched by the user.

(Ejection Head and Drug Tank)

An example of the constitution of ejection head 1 and drug tank 2 of the drug ejection apparatus of the present invention is described below with reference to FIGS. 5 to 7.

Figure 5:
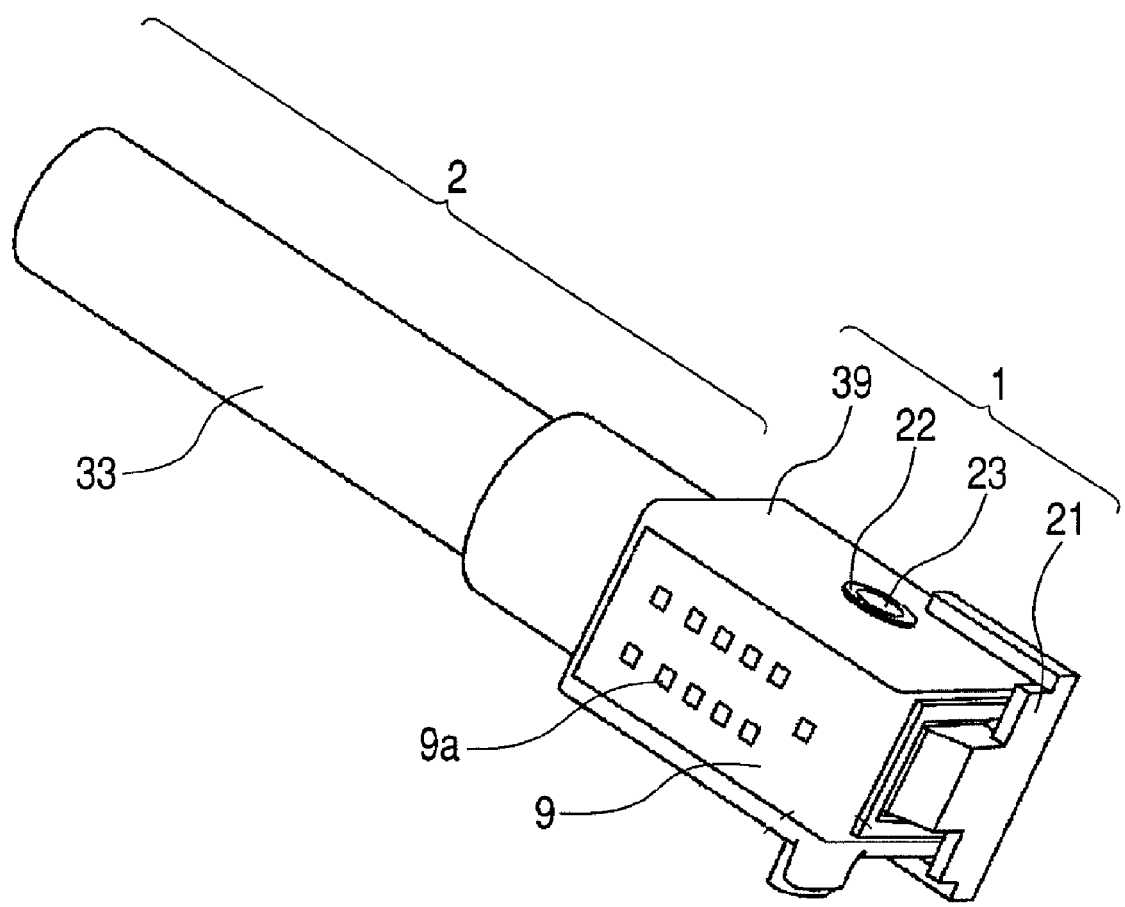
FIG. 5 illustrates perspectively an external appearance of ejection head assembly 1 with drug tank 2.
Figure 6:
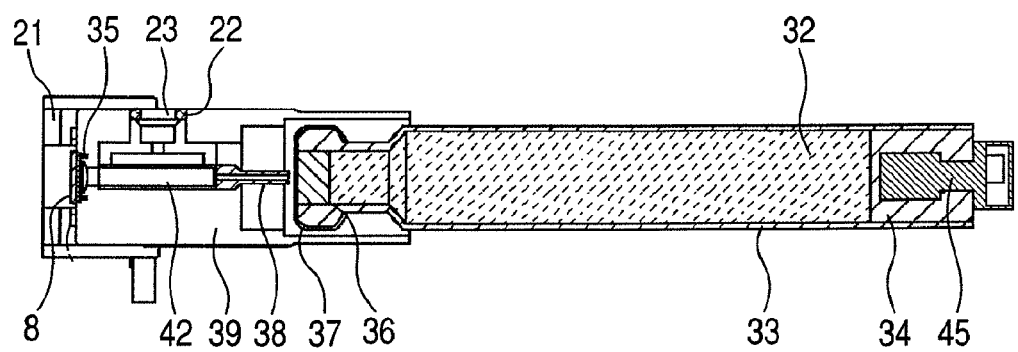
FIG. 6 is a principal sectional view of the parts illustrated in FIG. 5 before connection of ejection head 1 with drug tank 2.

FIG. 5 illustrates perspectively an external appearance of ejection head 1 with drug tank 2. FIG. 6 is a principal sectional view of the parts illustrated in FIG. 5 before connection of ejection head 1 and drug tank 2. FIG. 7 is a principal sectional view of the parts after connection of ejection head 1 with drug tank 2.

Figure 8:
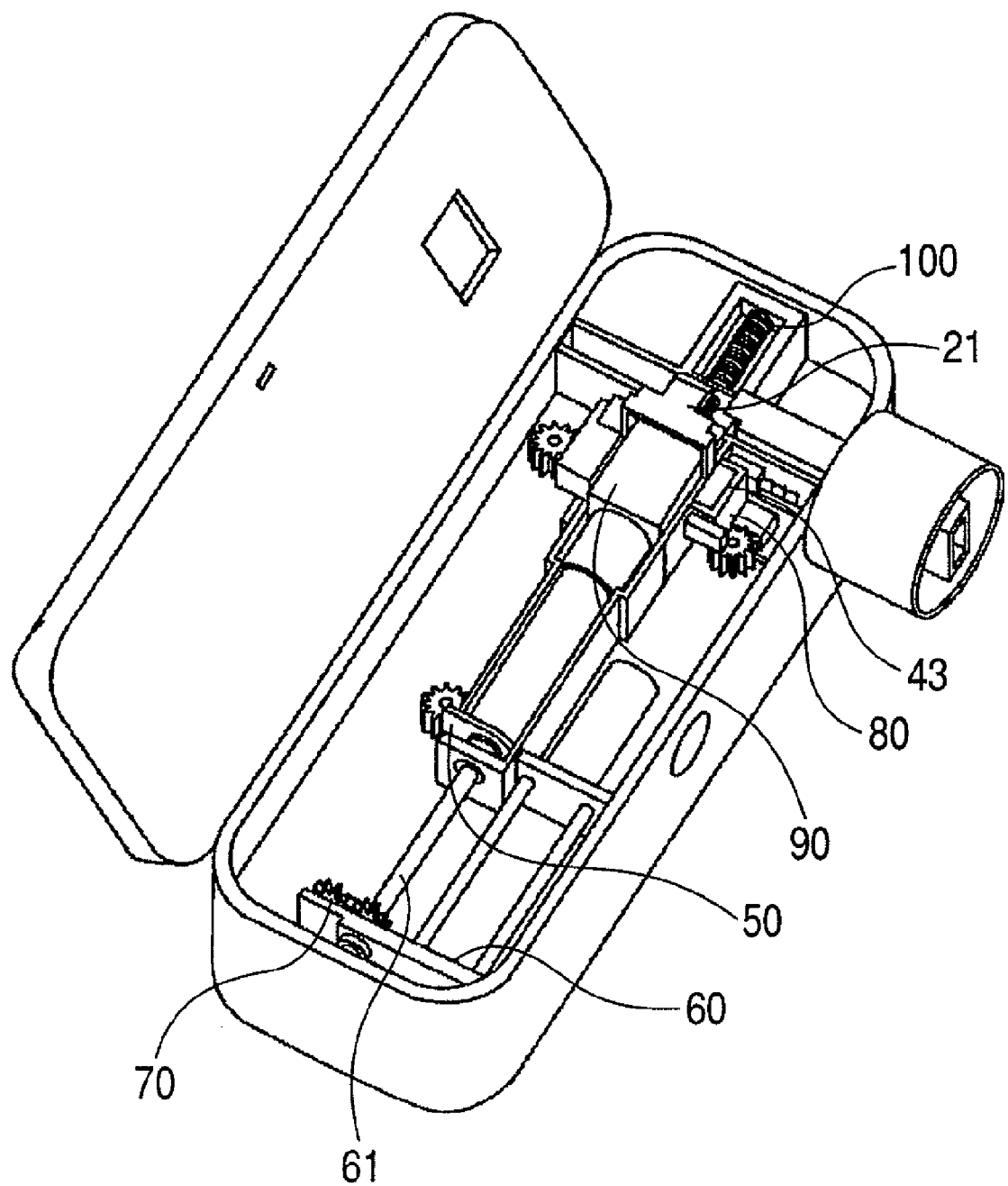
FIG. 8 illustrates perspectively the inside parts of the apparatus with drive-unit-protecting cover 31 of FIG. 4 removed.

Ejection head assembly 1 is constituted of the elements as below. Ejection head 8 having plural ejection ports is fixed and supported in casing 39, and inside the casing, hollow needle 38 is placed for supplying the drug from drug tank 2 to ejection head 8. Liquid drug flow path 42 for delivering drug 32 through hollow needle 38 to ejection head 8 is branched to pressure detection port 23 for measuring the inside pressure in liquid drug flow path 42. Pressure detection port 23 has sealing member 22 for preventing pressure leakage on connection with pressure sensor 3 (FIG. 8). After the connection, the pressure in the drug tank can be measured with this constitution since the pressure in the liquid drug flow path is approximate to the pressure in the glass container.

In ejection head 8, a heater is provided as the ejection energy-generating element near the ejection ports, and the heated drug is ejected by bubbling of the drug through the ejection ports. Electric connection face 9a and electric wiring part 9 for supporting the connection face are also provided. Through electric connection face 9a, an electric power is supplied from rechargeable battery 29 (FIG. 10) as a secondary battery held in the main body of the inhalation apparatus.

For protecting ejection head 8 before installation on the main body, head-protecting lever 21 having drug absorbent 35 is placed in contact with the ejection port face of ejection head 8. This lever is withdrawn at the time of the ejection to communicate the ejection port with the air flow path.

Drug tank 2 is constituted of the elements as below. The drug tank has glass vessel 33 for holding the drug. One end of glass vessel 33 is pinched with a fixed rubber stopper 36 by aluminum clamp 37, and the other end of the glass vessel 33 is closed by movable rubber stopper 34 inserted therein to intercept the drug from the outside air. On connection of ejection head assembly 1 with drug tank 2, the inside of the glass vessel is intercepted from the outside air except the ejection ports of ejection head 8. With this constitution, the drug tank is closed and the deterioration and concentration change of the drug is minimized.

Figure 7:
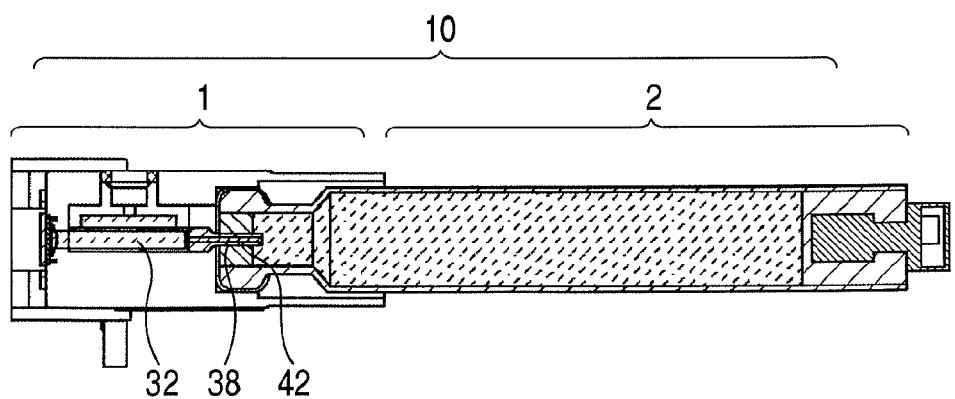
FIG. 7 is a principal sectional view of the parts illustrated in FIG. 5 after connection of ejection head 1 with drug tank 2.

Ejection head assembly 1 and drug tank 2 are communicated by pressing drug tank 2 into ejection head assembly 1 as illustrated in FIG. 7 to allow hollow needle 38 to penetrate through fixed rubber stopper 36. Drug 32 is filled into ejection head 8 by pushing movable rubber stopper 34 into the tank.

Ejection head assembly 1 and drug tank 2 are preferably incorporated into drug cartridge 10, before the communication of the two parts, for convenience for installation by the user to the main body of the inhalation apparatus.

(Inside Parts of Main Body of Apparatus)

FIG. 8 illustrates perspectively the inside parts of the apparatus with drive-unit-protecting cover 31 of FIG. 4 removed.

In the inside of the apparatus, thrusting unit 50 is provided which connects drug tank 2 with ejection head assembly 1 to form drug flow path 42. On the other side of drug tank 2, rubber stopper-displacing unit 60 is placed which displaces movable rubber stopper 34 within glass vessel 33 to change the inside volume of drug tank 2. The piston rod is displaced by rotating screw-shaft motor 64 (FIG. 9) having a screw shaft of rubber stopper-displacing unit 60. To prevent fall-out of rubber stopper joint 45 and piston rod 61, piston rod-rotating unit 70 is provided for hooking. On one side of drug cartridge 10 (a package of ejection head assembly 1 and drug tank 2), pressure sensor-connecting unit 80 is provided for connecting pressure sensor 43 to pressure sensing port 23. Ejection head 8 is protected by head-protecting lever 21. Ejection face is decapped by withdrawing head-protecting lever 21 by protecting lever-withdrawing unit 90. Above the ejection head, head capping unit 100 is provided which prevents drying and dust adhesion in ejection head 8 mounted on the main body.

Figure 9:
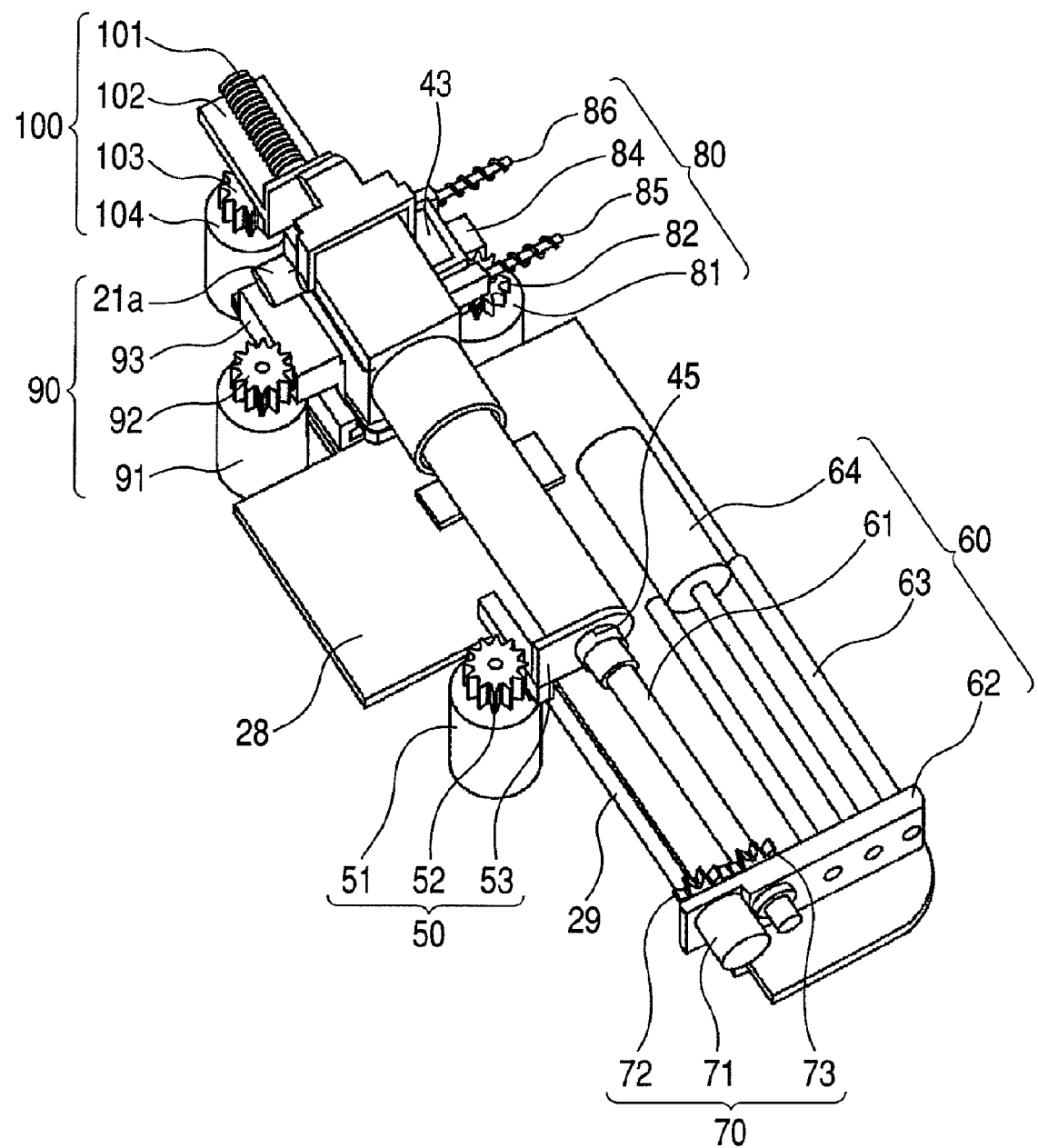
FIG. 9 illustrates perspectively the inside mechanism of the apparatus illustrated in FIG. 8 with the outside covers removed.

FIG. 9 illustrates perspectively the inside mechanism of the apparatus illustrated in FIG. 8 with the entire of the outside casing removed. Thrusting unit 50 is constituted of motor 51, pinion 52, and thrusting rack plate 53: the motor 51 generating a driving force for thrusting the drug tank, the pinion 52 being fitted to the shaft of the motor 51, and the rack plate 53 having a rack-shaped part for engaging with the pinion 52. Rack plate is placed to push the rear end of glass container 33.

Next, rubber stopper-displacing unit 60 is described. Screw-shaft motor 64 having a main shaft screwed is fit to piston rod-connecting plate 62 having a corresponding female screw. Guide shaft 63 is placed on both sides of the screw-shaft to guide the sliding of piston rod-connecting plate 62 without swinging. Thereby, the rotational driving force of screw-shaft motor 64 allows piston rod 61 to slide to displace movable rubber stopper 34 connected through rubber stopper joint 45.

Piston rod-reversing unit 70 is attached to piston rod-connecting plate 62. Piston rod-reversing unit 70 transmits the driving force of piston rod-reversing motor 71 and reversing motor gear 72 fitted to the motor shaft to piston gear 73 to rotate the piston rod. Piston rod 61 is engaged to movable rubber stopper joint 45. Movable rubber stopper 34 is pushed into or pulled out of glass tube 33 by the rotation of piston gear 73 to change the volume of the drug in the glass tube.

Control base plate 28 is placed under drug cartridge 10, and thereon drive control section 4 containing CPU, ROM, and RAM is provided for control of the main body including control of the driving motors, and change of the ejection conditions in accordance with the measured pressure.

Further, under control-base plate 28, battery 29 is placed as the source of the energy for driving the motors and ejection of the drug. Thereby, the drug can be ejected for inhalation with this main body independently and simply at any place.

Pressure sensor connecting unit 80 is described below. This unit allows pressure sensor 43 to slide for connection to or disconnection from pressure sensing port 23 of casing 39. This pressure sensor connecting unit 80 has connection rack 84. This connection rack converts the rotation force of connection motor gear 82 fitted to the motor main shaft of motor 81 to the force for sliding movement of the sensor. The driving force transmitted to connection rack 84 having a holder of pressure sensor 43 drives the sensor to slide away from casing 39. That is, motor 81 serves to disconnect the sensor. For the connection, pressure sensor is pressure-connected by pressure of pressing spring 86 for pressure sensor connection attached to periphery of connection rack guide bar 85 for guiding the movement of connection rack 84. Thereby, pressure sensor 43 is kept connected with the power source disconnected, and the inside pressure of the drug tank can be monitored during non-use storage state.

Lever-withdrawing unit 90 for withdrawing the head-protecting cover is described below. Pinion 92 fitted to the main shaft of motor 91 is engaged with protection lever rack 93 having a rack shape. Thereby protection lever rack 93 is slided to flip up withdrawing protrusion 21a at the end of head protection lever rack 21 to turn head protection lever 21 to bare ejection head 8. Protection lever-withdrawing unit 90 can be driven only when drug cartridge 130 is loaded.

Head-capping unit 100 is described below. Motor 104 is capable of sliding capping plate 102 by engagement of pinion 103 fitted to the motor shaft with the rack provided on the lower face of capping plate 102. Capping motor 104 is driven only when capping plate 102 is withdrawn. Ejection head 8 is capped by pressing force of capping spring 101. Therefore the head can be capped with the power source turned off. That is, head-capping unit 100 is driven only at the time of ejection from ejection head 8, whereas the head is capped to close the head to prevent drying at the time of non-ejection.

(Example of Use of Inhalation Apparatus)

Figure 10:
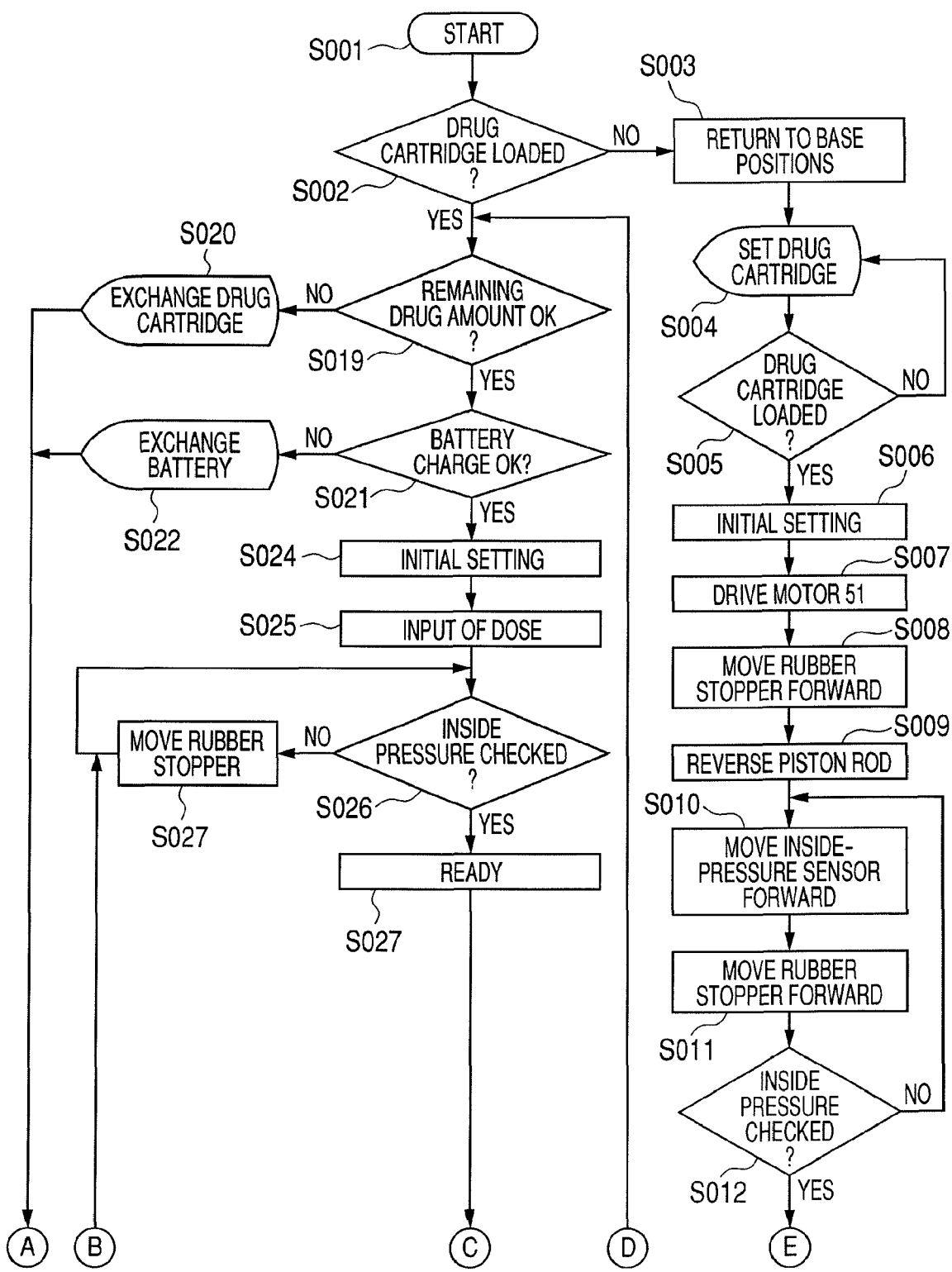
FIG. 10 is comprised of FIGS. 10A and 10B illustrating a flow chart of operation for use of the inhalation apparatus.

An example of use of the inhalation apparatus is described with reference to the flow chart shown in FIG. 10.

The master power switch is turned by the user on to make the apparatus ready for use (Step: S001). After the start of the operation of the apparatus, the loading of drug cartridge 10 is checked (S002). In the absence of the cartridge, the operation units (thrusting, rubber stopper movement, piston rod rotation reversal, pressure sensor connection, head protecting lever withdrawal, and head capping) are returned to respective base positions (S003) to make ready for drug cartridge 10 loading. Then a notice is displayed of the absence of drug cartridge 10 (S004) to urge the loading of drug cartridge 10. The loading of cartridge 10 can be detected, for example, in the ejection by a thermal jet system, by the resistivity of the heater placed in ejection head 8.

After detection of the loading of drug cartridge 10 (S005), initial setting is made (S006). After initial setting of S006, motor 51 is driven to communicate ejection head assembly 1 and drug tank 2 (S007). Thereby drug flow path 42 is formed for the flow of the drug through hollow needle 38 into ejection head 8. Then piston rod 61 is moved toward movable rubber stopper 34 in a certain distance for contact with rubber stopper 34 (S008). The term "certain distance" herein signifies the distance of the movement to cause contact of the front end of piston rod 61 with the movable rubber stopper. This movement distance can be controlled readily by the number of the sending steps since a stepping motor is employed as the screw-shaft motor 64. Next, piston rod reversing motor 71 is driven to turn the piston rod by an angle of 90° to engage the tip of the piston rod with rubber stopper joint 45 (S009). Then motor 81 is driven to move pressure sensor 43 forward (S010). Pressure sensor 43 is allowed to fit to pressure sensing port 23 tightly with sealing member 22 not to cause pressure leakage. The force of the adhesion between sealing member 22 and pressure sensor 43 is produced by pressure spring 86 for connection.

Figure 11:
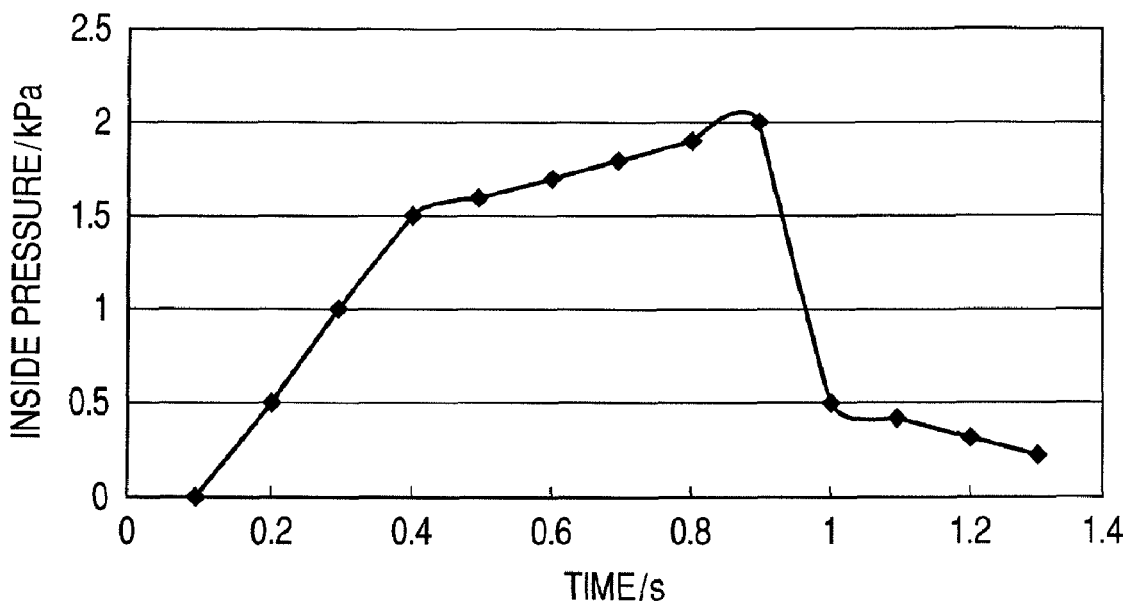
FIG. 11 is a graph showing a change of inside pressure in the drug tank during drug filling.

In the next step, drug 32 is filled into ejection head 8. In this step, piston rod 61 is driven forward to displace movable rubber stopper 34 so as to decrease the inside volume of glass container 33. Thereby drug 32 in glass container 33 is allowed to flow through drug flow path 42 into ejection head 8 to push out the air from drug flow path 42 through the ejection ports to fill ejection nozzle 8 with the drug (S011). However, since the inside diameter of ejection nozzle 1a is as small as 3 μm, the drug does not come out of the nozzle immediately and the pressure in the drug flow path and the glass tube begins to rise. The change of the pressure is measured and is fed back for control of the position of the movable rubber stopper 34 (S012). FIG. 11 shows an example of the change of the pressure in the drug tank during the drug filling. With forward movement of piston rod 61, the inside pressure rises gradually to exceed a pressure of 1.5 kPa. With the ejection nozzle of 3 μm diameter, the drug is known experimentally to leak out at about 2 kPa. Therefore, the feeding speed of screw-shaft motor 64 is lowered to meet the liquid drug leakage. Further forward movement of piston rod 61 causes sudden rise of the inside pressure differently from the previous pressure change. Screw-shaft motor 64 is stopped at this point (S013). The pressure at this point is about 2 kPa as intended. At about 2 kPa, the meniscus of the liquid drug is broken and the drug begins to leak through ejection nozzle 8 even though the motor is stopped. The leakage of the liquid drug causes sudden drop of the inside pressure down to about 0.2 kPa. As mentioned above, the motor is stopped quickly to meet the sudden pressure change immediately before the break of the meniscus to minimize the leakage of the drug to decrease the waste of the drug. In other words, for sure leakage by control of feed by piston rod 61 only, the feed rate should be made higher, which will cause increase of the waste of the drug.

The drug which has leaked out is sucked and absorbed by drug absorbent 35 placed inside the head-protecting lever. Then head-protecting lever 21 is turned from the surface of ejection head 8 by an angle of 90° by driving motor 91 to move the head-protecting lever upward above the upper face of casing 39 (S014). Thereafter, ejection for recovery may be conducted to push out the drug remaining on the ejection head face (S015). The amount of the ejection in the recovery ejection may be about 1/10 of the main ejection. Next, rubber stopper 34 is displaced to enlarge the inside volume of the glass tube by rotating reversely piston rod 61 to adjust the inside pressure (negative pressure) in drug container 33 and drug flow path 42 to be appropriate to the ejection (S016). Instead, for the ejection recovery, the inside pressure can be changed by ejection of the drug, similarly as by reverse rotation of piston rod 61. However, to decrease the waste of the drug, the recovery ejection is minimized and the inside pressure is adjusted by displacement of the rubber stopper 34. The initial filling is completed when the inside pressure has been adjusted to −0.5 kPa±0.1 kPa (S017, S018).

After completion of the initial filling, the operation is returned to ejection mode S019 to check the amount the remaining drug. When the amount of the remaining drug is not sufficient for one inhalation operation, the notice is displayed (S020), and the power source is turned off (S038).

When a sufficient amount of the remaining drug, the charge of battery 29 is checked (S021). When the charge is not sufficient, a notice is displayed to exchange or recharge the battery (S022) and the power source is turned off (S038). When the remaining charge of the battery is sufficient at least for one inhalation, the initial setting is conducted (S024).

After the initial setting, the drug dose is input in the step S025. Although the user may input the dose by himself, usually the dose of a data prescribed by a medical doctor is set preliminarily. However, in some cases, for example, to use insulin as the liquid drug, the user adjusts the data in consideration of the calorie intake and calorie consumption. In such a case, the dose is set by touching setting buttons 11 to 14 by watching display unit 15 (FIG. 3).

After the input of the dose, the inside pressure of drug tank 2 is measured and checked to be ready for the ejection (S026). If the pressure is out of the appropriate range, screw-shaft motor 64 is driven to move the piston rod to adjust the inside pressure to be in the appropriate range (S027) for inhalation by the user.

On start of the inhalation by the user, the pressure in air flow path 7 becomes negative. Therefore the user's inhalation is detected by detecting the negative pressure by a pressure sensor. On detection of a prescribed negative pressure, the drug ejection is started (S028).

At the initial stage of the ejection, movable rubber stopper 34 is at a fixed position (S029) for measuring precisely the drug ejection performance. The pressure change by the initial drug ejection can be measured precisely with movable rubber stopper 34 fixed (S030), even if the amount of initial ejection is small. By comparing this pressure change with the preliminary calibration of the pressure change as a function of the amount of ejection, the ejection performance at the moment can be estimated. Thereby, the ejection driving conditions can be corrected for ejection of the rest of the drug in an intended time length for the prescribed amount of the inhalation.

Figure 12:
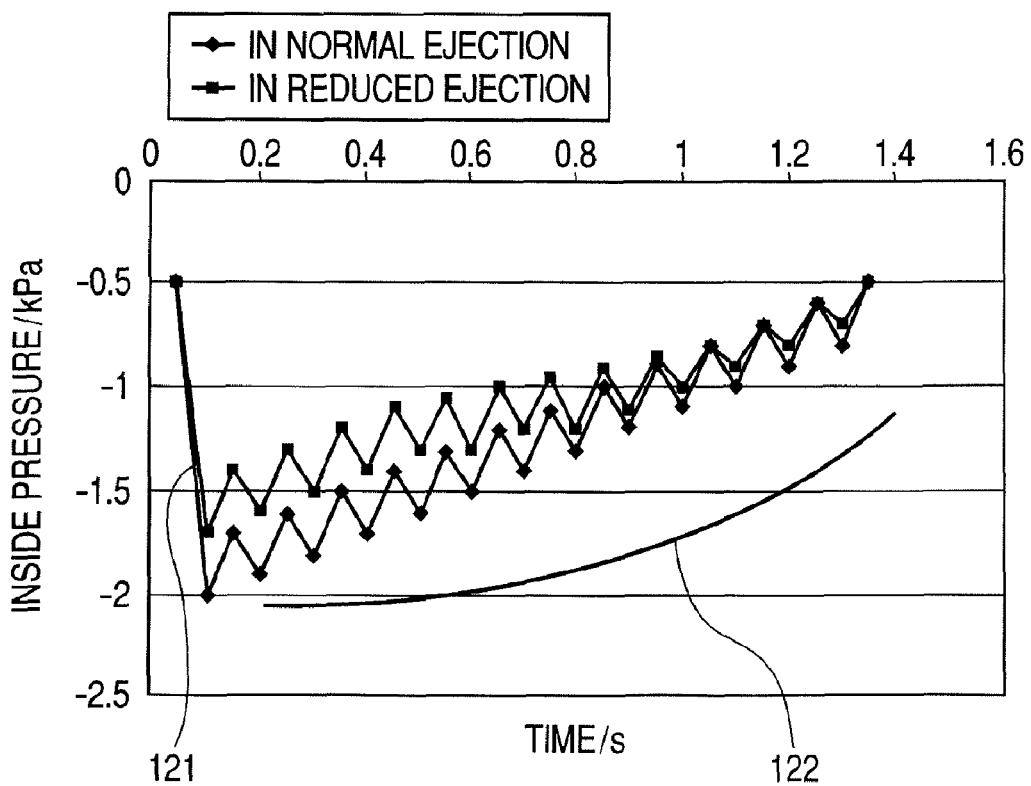
FIG. 12 is a graph showing a change of the inside pressure in the drug tank during the drug ejection.

FIG. 12 shows change of the inside pressure in the drug container during the ejection. In this example, the drug container is a glass container having an inside volume of 2 mL and an inside diameter of 6.8 mm. Therein a movable rubber stopper is inserted which has a Shore-A hardness of 50°, an outside diameter of 7.2 mm, a length of 6 mm, and having three encircling ridges. The initial stage of the ejection was conducted to eject 1/10 of the entire ejection amount under the conditions of the normal full ejection performance. FIG. 12 shows two examples: ejection in a normal state, and ejection by a nozzle having a lower performance owing to nozzle clogging. With the normal state of the nozzle, at the initial stage of ejection, the inside pressure in the container changed by −1.5 kPa from the initial pressure, whereas with the nozzle of a lower performance, the inside pressure changed by only −1.2 kPa. That is, the ejection performance dropped by a factor of 1.2/1.5. With the nozzle of lower performance, in the initial ejection stage, only 8% ((1/10)×(1.2/1.5)=0.08) of the total ejection amount is ejected. (Total ejection amount)= (Ejection amount in initial ejection)+(Ejection amount in main ejection). Therefore, in the later main ejection stage, the ejection conditions are adjusted to eject 92% of the intended total amount (S031).

$$(\text{Ejection Correction Factor}) = [1 - (1/10)(12/15)]/[1 - (1/10)(12/15)] = 1.2778$$

Thus, with the driving frequency, pulse width, and driving voltage kept unchanged, the ejection duration is made longer than the initial setting by a factor of 1.2778 to eject the intended entire amount of the drug. The ejection rate is nearly in a linear relation with any of the driving frequency, the pulse width, and the driving voltage. Therefore, any one of the driving conditions (frequency, pulse width, driving voltage) may be changed without changing the ejection time length, or one or more of the conditions may be changed in combination. On completion (S037) of the ejection (S032) under appropriately adjusted ejection conditions, the power source is turned off (S038). During the main ejection, movable rubber stopper 34 is slided suitably not to cause an excessive negative pressure in the drug tank owing to decrease of the remaining liquid drug to moderate the negative pressure (S034). Examples of the pressure change are shown in FIG. 12.

When the ejection performance has become lower and the ejection period is adjusted to be longer, the prescribed entire amount of the drug for one inhalation can not be ejected during one inhalation operation by the user. Therefore, the ejection period is preliminarily set, in consideration of one inhalation period of the user, not to be too long, the adjusted ejection period including the initial ejection time when the initial ejection is utilized for the inhalation. In such a case, the ejection frequency, the ejection pulse width, or the driving voltage is preferentially changed.

Next, the treatment is described in the case where the user has stopped the inhalation halfway during the prescribed ejection period (S035), or in the case where the upper limit of the ejection period length is not set as mentioned above and the user cannot inhale the entire ejected amount of the drug by one inhalation operation. The start and finish of the inhalation by the user can be monitored in-situ by measurement of the negative pressure in air flow path 7. Therefore, when the inhalation by the user comes to be not sensed by the pressure sensor, controller 4 stops the drive of the ejection energy-generating element, because ejection of the drug during interruption of the inhalation is not preferred. At this time, the amount of the ejection before the stop of the ejection is calculated, and deficiency for the entire ejection amount is calculated (S036). The amount of the ejection can be estimated from the movement of movable rubber stopper 34, or can be estimated by the number of the ejected droplets multiplied by the volume of the one drop. The deficiency of the inhalation amount is informed to the user to urge the second-time inhalation. On sensing of the second-time inhalation, the ejection energy-generating element is started. In this second-time ejection, the ejection performance may be checked by preliminary ejection before the second-time ejection. When the time interval is large before the second-ejection, this check of the ejection performance is effective since the ejection performance may vary during the interruption of the ejection.

The confirmation of the ejection performance by ejection with movable rubber stopper 34 fixed may be conducted not only at the initial ejection but also plural times during the one sequence of the ejection. The method of adjustment and control is the same as that in the initial ejection, the accuracy of the amount of the ejection can be improved by the additional adjustment ejection. This plural-time adjustment is suitable for the drug which can recover a clogged nozzle by ejection.

(Preservation Mode)

Drug tank 2 has a capacity for holding the drug in an amount for several times of inhalation operation. Therefore the apparatus may be stopped with the power source turned off with drug cartridge 10 kept loaded to the main body until the next use. The mode in this period is defined as a preservation mode.

Figure 10B:
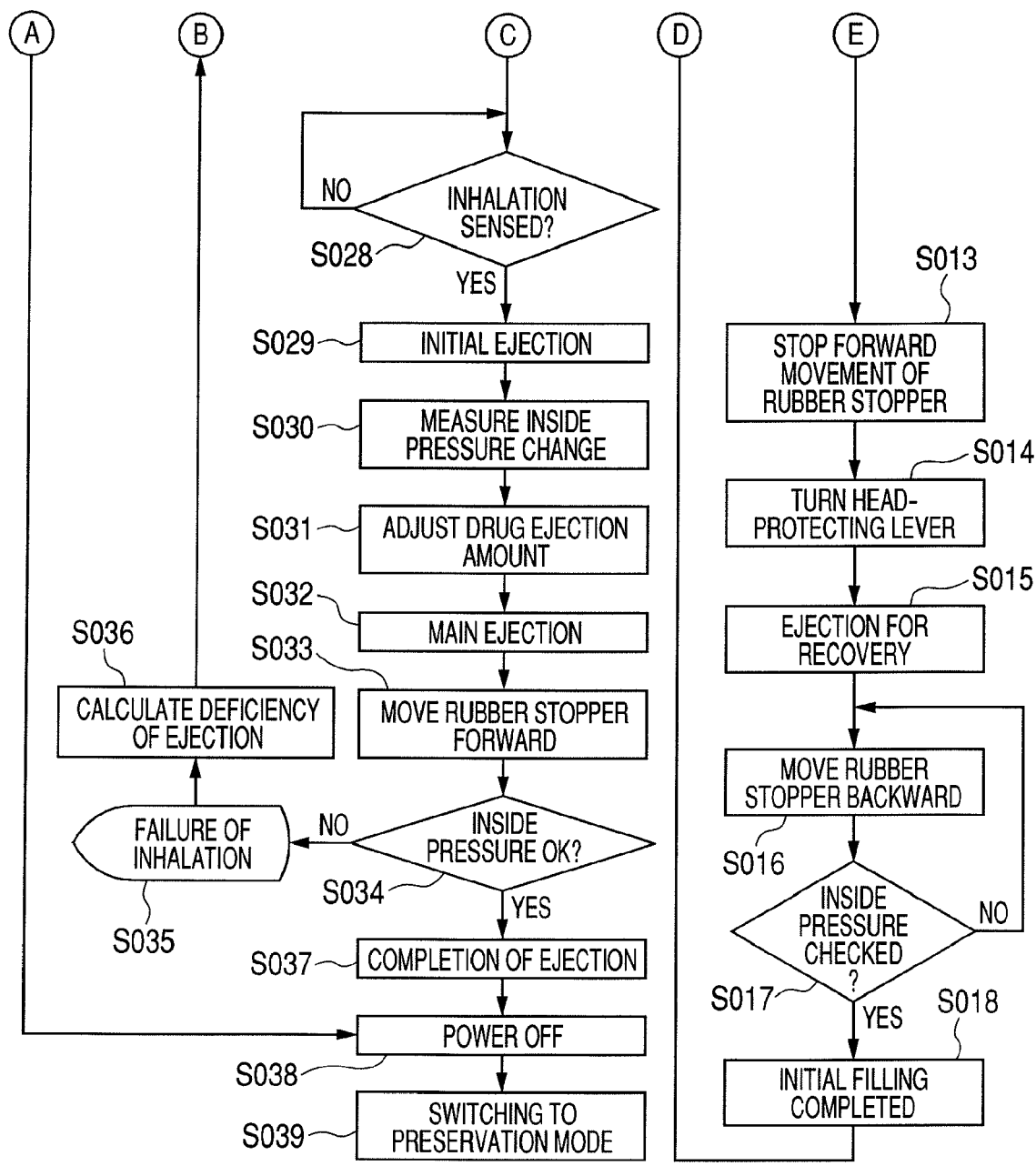
Figure 13:
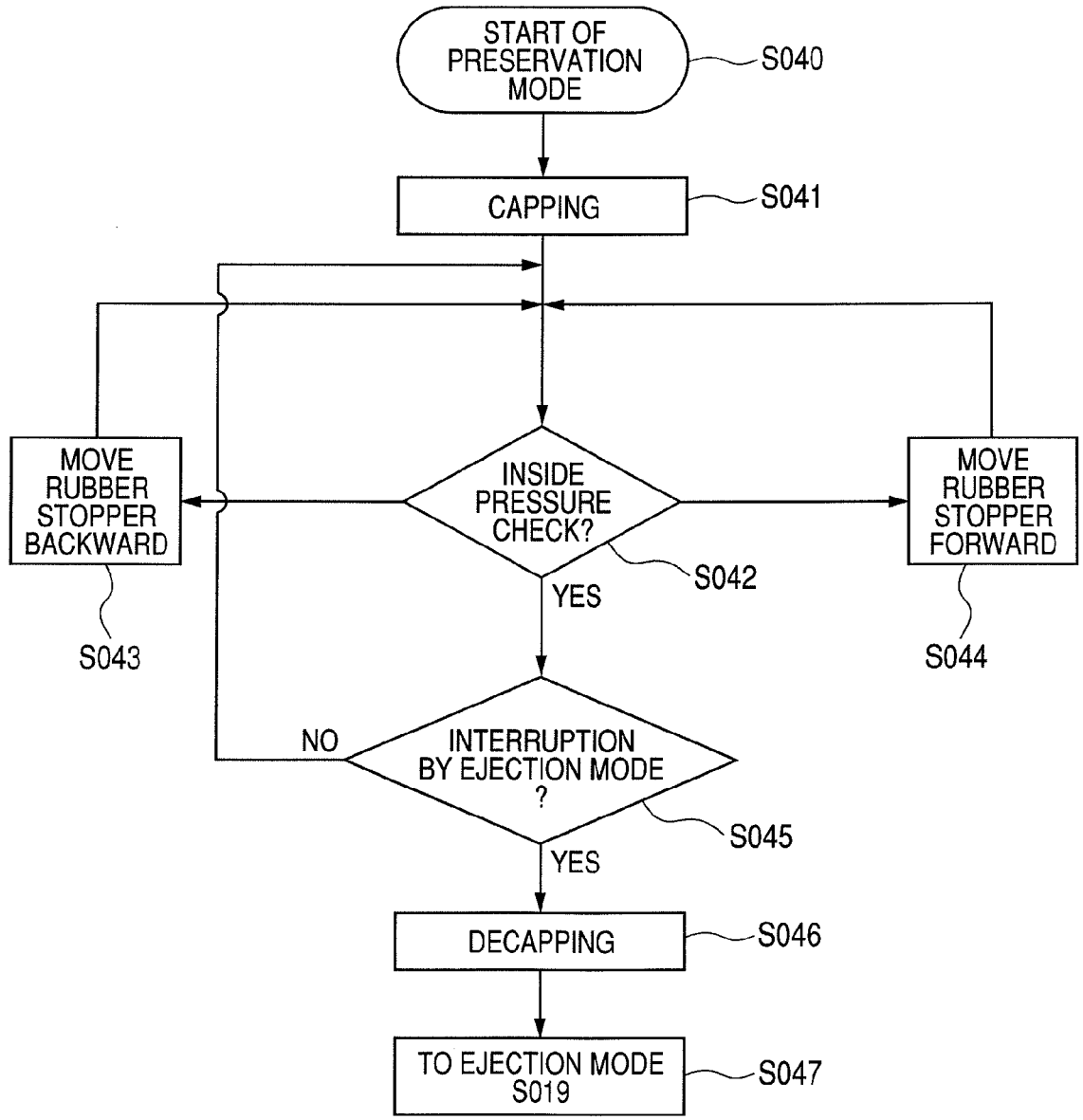
FIG. 13 is a flow chart of operation in a preservation mode.

In the preservation mode, environmental changes can cause change in the inside pressure in the drug tank 2 by expansion or constriction of the liquid drug and variation of the atmospheric pressure. FIG. 13 shows an operation flow chart in the preservation mode. In FIGS. 11A and 10B, by turning off the power source (S038), the mode is switched automatically to the preservation mode (S039) to start the preservation mode (S040).

In the preservation mode, firstly motor 104 is driven to move capping plate 102 to the side of drug cartridge 10 to cap tightly the face of ejection head 8 (S041). Then the pressure in drug tank 2 is measured by pressure sensor 43 to compare the pressure with the prescribed preservation pressure range (S042). When the pressure is higher than the intended preservation pressure range, rubber stopper 34 is moved in the direction (backward) by driving rubber stopper-moving unit 60 is driven to enlarge the inside volume of glass container 33 (S043). This movement of the rubber stopper is repeated to bring the inside pressure in drug tank 2 into the intended preservation pressure range. Conversely, when the pressure is lower than the intended preservation pressure range, rubber stopper 34 is moved in the direction (backward) to reduce the inside volume of glass container 33 by driving rubber stopper-moving unit 60 (S044). The rubber stopper is moved repeatedly to bring the inside pressure in drug tank 2 into the intended preservation pressure range. When the inside pressure is changed by a change in the environment out of the intended preservation range, the steps of S042, and S043 or S044 are repeated to bring the pressure to the prescribed range. At the pressure within the prescribed range, the apparatus is ready for interruption by the ejection mode (S045). When the mode is interrupted by the ejection mode, motor 104 is driven to withdraw capping plate 102 from the face of ejection head 8 to constitute a part of the air flow path (S046). With the periphery conditions becomes ready for the ejection, the mode is converted to the ejection mode of S019 (S047).

The inside pressure need not be continuously monitored, but may be monitored intermittently with intervals. The time interval is decided in consideration of possible change in actual environmental conditions. For example, on board on an air plane, the atmospheric pressure can change by about 700 hPa in about 30 minutes, which may be the largest possible change in practical use. The possible largest change in the temperature may be may be about 30° C., which can be caused when the apparatus is brought from the outdoor into a warmed room.

In place of checking the inside pressure in the drug tank, an atmospheric pressure sensor or a temperature sensor may be equipped in the interior of the apparatus main body. In the preservation mode, only a part of the circuit of monitoring sensors is working and most of the main body is in a sleep state. For energy saving, the wake-up circuit is allowed to work to start the control unit preferably only when a change is detected in any of the sensors.

(Other Pressure Sensing Means)

Figure 14:
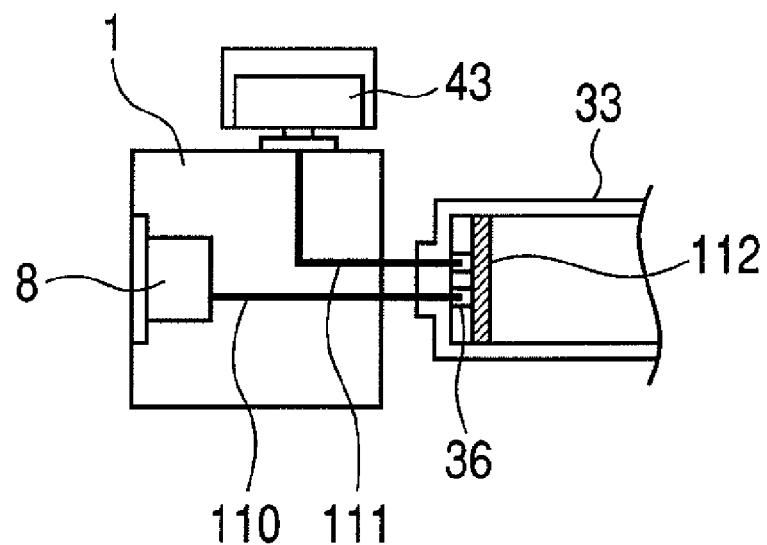
FIG. 14 illustrates schematically an embodiment of measurement of the inside pressure in drug tank 2.

FIG. 14 illustrates schematically another system for monitoring the inside pressure in drug tank 2. Hollow needle 110 allows ejection head 8 to communicate with the inside of glass container 33. Hollow needle 111 forms a flow path between pressure sensor 43 for sensing the inside pressure and glass container 33. In this embodiment, the hollow needle connected to pressure sensor 43 is separated from the drug flow path for filling the liquid drug into the head. Thereby the air existing between container 33 and pressure sensor 43 will not reach the nozzle of head 8, and interruption by the drug ejection by the air is prevented. Mesh filter 112 is placed on the front face of fixed rubber stopper 36.

Figure 15:
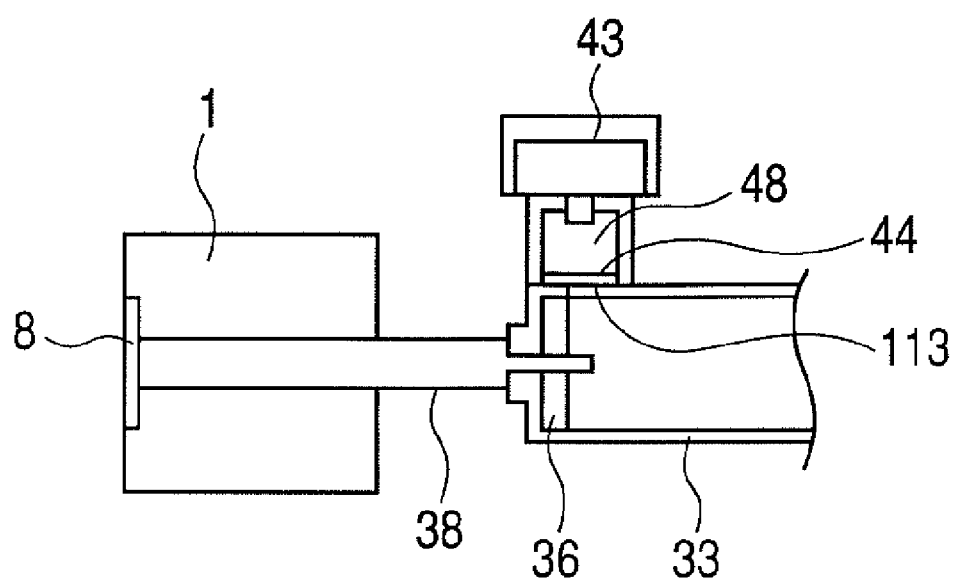
FIG. 15 illustrates schematically another embodiment of measurement of inside pressure in drug tank 2.

FIG. 15 illustrates schematically still another system for monitoring the inside pressure in drug tank 2. Pressure sensing port 113 is provided at the end of glass container 33 for sensing the inside pressure. Pressure sensing film 44 is adhered at the periphery so as to seal pressure sensing port 113. The center portion of the film is deformable by the inside pressure change in glass container 33. Pressure sensing film 44 is a flexible thin film made of polyethylene as the base material and is coated by vapor-deposited aluminum, the non-coated polyethylene film side facing to glass container 33 and the aluminum-deposited side facing to pressure sensor 43. This thin film has both properties of high drug resistance of the polyethylene and gas barrier property of the aluminum. A change of the pressure inside the glass container deforms pressure sensing film 44 to change the pressure of air layer 48 in the space between pressure sensor 43 and pressure sensing film 44. This change of the pressure is sensed by pressure sensor 43. This pressure sensing method is the most suitable for the drug which should not be contaminated by a disinfectant since the drug is not brought into contact with air. Otherwise, a displacement sensor may be employed in place of pressure sensor 43 for direct measurement, or a strain type load sensor may be employed to detect the displacement of the thin film.

INDUSTRIAL APPLICABILITY

The drug ejection apparatus of the present invention is useful for various application field other than the drug inhalation, such as an ejection apparatus for spraying a fragrance material, and an inhalation apparatus for inhaling a tasty thing like nicotine. Like this, the drug-ejection apparatus of the present invention is applicable to various uses for sure and sanitary ejection.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-014458, filed Jan. 25, 2008, which is hereby incorporated by reference in its entirety.

What is claimed is:

1. A drug ejection apparatus comprising:
   a drug ejection assembly having an ejection port and an element for generating energy for ejecting a drug through said ejection port;
   a drug container connected with said drug ejection assembly for holding the drug;
   a pressure sensor unit for sensing a change of the inside pressure of said drug container caused in correspondence with an amount of the drug ejected through said drug ejection assembly; and
   a drive control unit configured for correcting driving conditions of said drug element such that an amount of the drug in succeeding ejections is increased from a first prescribed amount when an output level of said pressure sensor unit on driving said element to perform an initial ejection under prescribed conditions is higher than a prescribed pressure, and for driving said element according to the corrected driving conditions.

2. The drug ejection apparatus according to claim 1, further comprising a pressurizing unit for pressurization of said drug container to decrease the volume of said drug container to effect a moderate decrease of the inside pressure caused by ejection of the drug.

3. The drug ejection apparatus according to claim 2, wherein the pressurization of said drug container by said pressurizing unit is stopped during driving of said element under prescribed conditions.

4. The drug ejection apparatus according to claim 1, wherein any of the driving conditions of said element including ejection frequency, ejection pulse width, driving voltage decided by said drive control unit is adjusted so that the ejection period is not longer than a prescribed period.

5. The drug ejection apparatus according to claim 1, wherein the apparatus comprises a sensor for sensing inhalation by a user, and driving of said element is stopped when the inhalation by the user comes to be not sensed by said sensor.

6. The drug ejection apparatus according to claim 5, further comprising a unit for measuring the amount of the ejected drug, and wherein said drive control unit decides the conditions for driving said element for ejecting the drug in an amount corresponding to the difference of the amount of the ejected drug from a second prescribed amount of the drug on stopping driving of said element.

* * * * *